United States Patent [19]
Kashanchi

[11] Patent Number: 5,775,498
[45] Date of Patent: Jul. 7, 1998

[54] HYPODERMIC NEEDLE STORAGE APPARATUS

[76] Inventor: Behnam Kashanchi, 450 N. Bedford Dr., Suite 209, Beverly Hills, Calif. 90210

[21] Appl. No.: 903,591

[22] Filed: Jul. 31, 1997

[51] Int. Cl.$^6$ .................................................. B65D 83/10
[52] U.S. Cl. .......................... 206/364; 206/367; 604/192; 604/263
[58] Field of Search .......................... 206/365, 366, 206/364, 367, 438, 363; 604/192, 263

[56] References Cited

U.S. PATENT DOCUMENTS

| | | | |
|---|---|---|---|
| 4,479,496 | 10/1984 | Hsu | 206/365 X |
| 5,020,665 | 6/1991 | Bruno | 206/366 |
| 5,439,453 | 8/1995 | Kashanchi | 206/365 X |

*Primary Examiner*—Jacob K. Ackun
*Attorney, Agent, or Firm*—Michael A. Painter

[57] ABSTRACT

An apparatus for storing a hypodermic needle before and after use. A pair of integral, cylindrical storage members are in parallel spaced relation to one another. The first storage member comprises a cylindrical housing closed at one end into which an unused, sterile hypodermic needle may be mounted. The hypodermic needle includes an enlarged, tubular hub which engages the open end of the first storage member. The second storage member includes a closed end and an open end. The cylindrical wall of the second storage housing is longitudinally severed from the open end of the second storage housing to a point substantially adjacent the closed end thereof. The open end of the second storage housing is adapted to frictionally engage the enlarged hub of the hypodermic needle. The longitudinal edges of the severed cylindrical wall of the second storage housing define a severed interface which will permit the hypodermic needle to be resheathed through the lateral opening in the wall of the second storage member.

6 Claims, 1 Drawing Sheet

HYPODERMIC NEEDLE STORAGE APPARATUS

BACKGROUND OF THE INVENTION

1. Field of the Invention.

The present invention generally relates to apparatus for storing and recapping hypodermic needles and, more particularly, those which will prevent inadvertent puncture wounds incurred when recapping the needle.

2. Prior Art.

It is well recognized that modern medical procedures make extensive use of hypodermic needles for the purpose of giving injections, blood transfusions and for taking blood samples from a patient. One of the most frequent problems which occurs as a result of using hypodermic needles, catheters and the like is the occurrence of inadvertent puncture wounds which are suffered by the practitioner while attempting to recap the hypodermic needle after use. Such inadvertent punctures often require treatment of the injury and, most importantly, in many cases require the treatment of illnesses or diseases that may result from the puncture wounds. Where injuries or illnesses occur from inadvertent puncture wounds, the user may be faced with unacceptable financial expendituresland the loss of employee time.

The problems incident to inadvertent puncture wounds cannot be underestimated. As is now recognized, one of the most deadly diseases known to man, the HIV virus, can readily be transmitted through the use of contaminated needles. In addition, diseases such as herpes, syphilis, malaria and tuberculosis may be contracted by inadvertent puncture wounds by a hypodermic needle which has been used on a patient. To address this significant problem, the prior art discloses numerous devices which attempt to prevent the occurrence of inadvertent puncture wounds while recapping or resheathing a used hypodermic needle.

One of the devices disclosed by the prior art to reduce the problem of inadvertent puncture wounds utilizes a housing having a central hole in a finger-protecting shield that allows a hypodermic needle to be inserted therethrough while being grasped during the recapping procedure. The major problem associated with this type of design is that the point of the hypodermic needle must, by necessity, be moved longitudinally with respect to the axis of the shield. Therefore, opposed lateral movement of the hypodermic needle relative to the finger-protecting shields may still result in an inadvertent puncture wound.

Another device taught by the prior art provides for covering and uncovering the hypodermic needle by relative lateral movement between he needle housing and the hypodermic needle. An elongated housing is provided with an open, elongated slot which permits insertion of the hypodermic needle into the housing and removal of the needle therefrom by relative lateral movement between the housing and the needle. The elongated slot in the housing is covered by a removable cover which, after removal, results in the exposed opening defined by the slot. The problem inherent in this device results from the open, elongated slot. Once the covering member has been removed from the elongated slot, the hypodermic needle may be inadvertently dislodged from the housing thereby providing for a continued risk of inadvertent puncture wounds.

U.S. Pat. Nos. 5,527,296 and 5,439,453 illustrate similar storage apparatus which are intended to provide containers for storing and recapping hypodermic needles. In both cases, the patents disclose storage apparatus which permit the reinsertion of a hypodermic needle by laterally inserting the needle into the storage apparatus through a severed portion of the longitudinal wall. The problems inherent in these devices relate to the unitary storage chamber and the complexity of the insertion mechanism. The devices disclosed by the prior art do not include an isolated storage chamber for maintaining the hypodermic needle in a sterile condition prior to use.

The present invention resolves those problems inherent in the devices taught by the prior art. The present invention provides a pair of integral, elongated housings. The first elongated housing includes a fully enclosed chamber into which the hypodermic needle is inserted and maintained in a sterile condition prior to use. The longitudinal wall of the second storage chamber is sliced or otherwise severed to create an opening along its longitudinal axis from the open end thereof. The open end of the second storage chamber is adapted to frictionally engage a portion of the hypodermic needle. The used, hypodermic needle is laterally inserted into the second storage housing through the severed wall. The hypodermic needle being maintained safely in place within the chamber of second storage housing through its frictional engagement with the second storage housing.

SUMMARY OF THE INVENTION

The present invention provides an apparatus for safely storing a hypodermic needle in a sterile condition prior to use and in its contaminated condition after use. A pair of cylindrical chambers are secured to one another, the longitudinal axes being in parallel spaced relation. The first storage chamber is open at one end and closed in the other. The open end is adapted to frictionally engage the elongated hub of the hypodermic needle. When the needle is in its sterile condition, it will be maintained safely within the first storage chamber through the frictional engagement between the elongated hub and the open end of the first storage chamber.

The second storage chamber has a closed end and an open end, the open end preferably being in opposition to the open end of said first storage chamber. The cylindrical wall of the second storage chamber is severed from the open end and extends downwardly in parallel spaced relation to the longitudinal axis of the second storage chamber. The open end is adapted to frictionally engage the elongated hub of the hypodermic needle. After the hypodermic needle has been used, it may be laterally inserted through the severed opening or interface in the cylindrical wall of the second storage chamber, the elongated hub thereof being frictionally engaged within the open end thereof.

It is therefore an object of the present invention to provide an improved hypodermic needle storage apparatus.

It is another object of the present invention to provide a hypodermic needle storage apparatus which minimizes the hazards resulting from inadvertent needle punctures.

It is still another object of the present invention to provide a hypodermic needle storage apparatus which maintains the hypodermic needle in a sterile condition prior to use and permits the hypodermic needle to be resheathed by relative lateral movement between a housing member and the needle.

It is still yet another object of the present invention to provide a hypodermic needle storage apparatus which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

DESCRIPTION OF THE PRESENTLY PREFERRED EMBODIMENT

Figure 1:
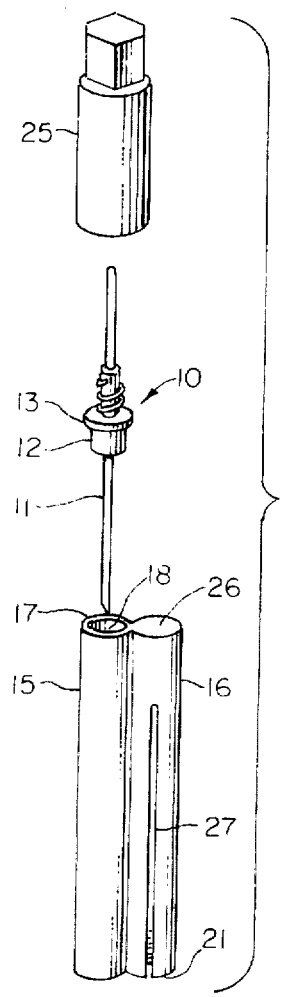
FIG. 1 is an assembly, perspective view of a hypodermic needle and the present invention storage apparatus.

The present invention hypodermic needle storage apparatus can be best seen by reference to FIG. 1 wherein an assembly of a hypodermic needle and a storage apparatus can be best seen. In its general form, a hypodermic needle 10 to be used with the present invention comprises the needle 11 and collar 12. A sealing, tubular hub 13 is typically used to align the hypodermic needle assembly 10 and is used to position the assembly 10 within the present invention storage apparatus.

Figure 2:
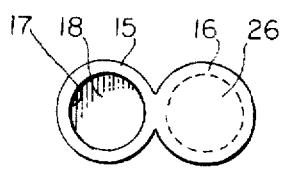
FIG. 2 is a top, plan view of the present invention hypodermic needle storage apparatus.
Figure 3:
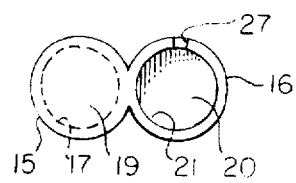
FIG. 3 is a bottom plan view of the present invention storage apparatus.

The present invention storage apparatus employs a first storage housing 15 and second storage housing 16 which enclose cylindrical chambers 18 and 20, respectively. First and second storage housings 15 and 16 are integral with each other and oriented in parallel spaced relation with one another. As can be best seen in FIG. 2 and FIG. 3, first storage housing 15 has an open end 17 defining an inner chamber 18 enclosed by closed end 19 (FIG. 3). Second storage housing 16 defines an inner cylindrical chamber 20. Second storage housing 16 preferably has an open end 21 which is opposed to open end 17 of first storage housing 15, the axially opposed end 26 being closed as shown in FIG. 2. Although the preferred embodiment of the present invention employs storage housings 15 and 16 with opposing open ends 17 and 21, respectively, it is understood the scope of the present invention includes housings wherein the openings thereto may be disposed at the same axial ends.

As stated hereinabove, it is an objective of the present invention to include a storage chamber for a hypodermic needle which will maintain the hypodermic needle in a sterile condition. As shown in FIG. 1, hypodermic needle 10 is adapted to be inserted within chamber 18 of first storage housing 15. Open end 17 of first storage housing 15 is adapted to frictionally engage tubular collar 12. To maintain hypodermic needle 10 in its sterile condition, after it is inserted within chamber 18, sealing cap 14 is disposed about sealing hub 13 to maintain a substantially hermetic seal.

Figure 5:
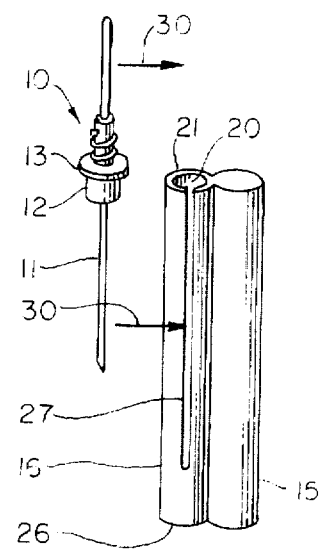
FIG. 5 is a schematic illustration showing the movement involved in recapping a hypodermic needle.
Figure 4:
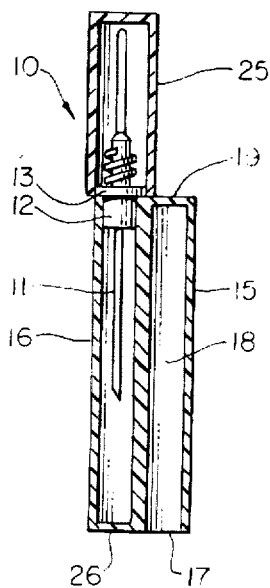
FIG. 4 is a cross-sectional view of a hypodermic needle and the storage apparatus in assembled condition.

The structure of the second storage housing 16 may be best seen by reference to FIGS. 3, 4 and 5. Second storage housing 16 comprises a cylinder defining an inner chamber 20. A closed end 26 is integral with the walls of second storage housing 16. As stated hereinabove, it is an objective of the present invention to permit the resheathing of the hypodermic needle assembly 10 by laterally moving the needle 11 relative to second storage housing 16. To accomplish this objective, the cylindrical wall of second storage housing 16 is severed longitudinally from open end 21 to substantially adjacent closed end 26. This creates a longitudinally disposed open interface 27 from open end 21 to a point substantially adjacent closed end 26.

The integral structure of first storage housing 15 and second storage housing 16 is constructed of a resilient thermoplastic material which may be deformed when a force is applied thereto, but will return to its undeformed, quiescent condition when the force is removed. When hypodermic needle 10 is in its unused state, it must be maintained in a sterile condition. In order to permit hypodermic needle assembly 10 to be maintained in a sterile condition, a hermetic seal must be created between tubular collar 12 and open end 17 of first storage housing 15. Open end 17 of first storage housing 15 is adapted to frictionally engage collar 12. The deformable resilience of first storage housing 15, when engaged with collar 12, will create the required hermetic seal. Once hypodermic needle assembly 10 is fully disposed within chamber 18 of first storage housing 15, sealing cap 25 may be disposed about sealing hub 13 to maintain the sterile condition of hypodermic needle assembly 10.

The operation of the present invention may be best understood by reference to FIG. 4 and FIG. 5. After hypodermic needle assembly 10 has been used, it must be presumed to be in a contaminated state. As can be seen in FIG. 5, interface 27 is adapted to laterally receive needle 11. To resheath hypodermic needle assembly 10, assembly 10 is moved laterally in a manner indicated by reference numerals 30. Once needle 11 is properly disposed within chamber 20, needle assembly 10 is urged downwardly into chamber 20 until the tubular collar 12 frictionally engages open end 21. In the same manner as described with respect to the insertion of hypodermic needle assembly 10 into chamber 18, the frictional engagement between open end 21 of second storage housing 16 and collar 12 will permit the needle assembly 10 to be safely stored. This frictional engagement will firmly position needle 11 along the longitudinal axis of second storage housing 16 thereby precluding inadvertent contact with the contaminated needle 11. Needle assembly 10 is fully recapped by slidably fitting sealing cap 25 upon sealing hub 13 in the same manner shown as FIG. 1.

It can therefore be seen the present invention provides an improved apparatus for storing and resheathing hypodermic needles. Prior to use, hypodermic needle assembly 10 is inserted within first storage housing 15, the needle remaining in a sterile condition as a result of the hermetic seal between collar 12 and open end 17 of first storage housing 15. When replacing the hypodermic needle after use, needle 11 may be inserted within second storage housing 16 by laterally urging needle 11 through interface 27, tubular collar 12 being frictionally engaged to open end 21 of second storage housing 16. The used hypodermic needle assembly 11 will be maintained in a safe condition as a result of the frictional engagement between collar 12 and open end 21 which will align needle 11 along the longitudinal axis of second storage housing 16. The structure of the present invention and its manner of operation avoids the necessity of moving the point of needle 11 in the direction of a hand of a user thereby precluding inadvertent puncture wounds.

I claim:

1. A hypodermic needle storage apparatus for use with a hypodermic needle assembly having a collar and a needle extending therethrough, comprising:

(a) a first cylindrical storage housing having an open end and an opposing closed end, said open end being adapted to frictionally engage the collar of the hypodermic needle assembly;

(b) a second cylindrical storage housing disposed adjacent said first cylindrical storage housing and having and outer wall defining an inner chamber and an open end and a closed end at axial ends of said outer wall, said open end being adapted to frictionally engage the collar of the hypodermic needle assembly, the outer wall of said second cylindrical storage housing being longitudinally severed from said open end to said second end and providing lateral access to the inner chamber for storage of the hypodermic needle assembly therein; and (c) a sealing cap adapted to be longitudinally disposed upon and received by the hypodermic needle assembly in opposition to the needle.

2. A hypodermic needle storage apparatus as defined in claim 1 wherein said first cylindrical storage housing and said second cylindrical storage housing are integral with one another, the longitudinal axes of said first cylindrical storage housing and second cylindrical storage housing being in parallel spaced relation to each other.

3. A hypodermic needle storage apparatus as defined in claim 2 wherein the open ends of said first and second cylindrical storage housings are in axial opposition to one another.

4. A hypodermic needle and storage assembly comprising:

(a) a hypodermic needle having a tubular collar and a needle extending axially therethrough;

(b) a first storage housing having a cylindrical outer wall defining an axially aligned inner chamber and an open end and a closed end in axial opposition to one another, said open end being adapted to frictionally engage said tubular collar;

(c) a second storage housing having a cylindrical outer wall depending from the cylindrical outer wall of said first storage housing, said cylindrical outer wall defining an axially aligned inner chamber and having opposed open and closed ends in axial opposition to one another, said open end being adapted to frictionally engage the tubular collar, the outer wall of said second storage housing having a severed interface from the open end thereof to substantially adjacent the closed end, said interface being parallel to the longitudinal axis of said second storage housing, said interface being adapted to laterally receive the needle for entry into the inner chamber of said second storage housing; and (d) a sealing cap adapted to be disposed upon the tubular collar in axial opposition to the needle.

5. A hypodermic needle and storage assembly as defined in claim 4 wherein the outer walls of said first storage housing and said second storage housing are integral with one another, the longitudinal axes being in parallel spaced relation.

6. A hypodermic needle and storage assembly as defined in claim 5 wherein the open ends of said first storage housing and said second storage housing are in opposition to one another.

* * * * *